US012667315B2

(12) United States Patent
Taal et al.

(10) Patent No.: US 12,667,315 B2
(45) Date of Patent: Jun. 30, 2026

(54) PHYSIOLOGICAL SENSORS WITH COMBINED SIGNAL OUTPUTS

(71) Applicant: Apple Inc., Cupertino, CA (US)

(72) Inventors: Adriaan J Taal, San Diego, CA (US); Amandeep Singh, San Jose, CA (US)

(73) Assignee: Apple Inc., Cupertino, CA (US)

( * ) Notice: Subject to any disclaimer, the term of this patent is extended or adjusted under 35 U.S.C. 154(b) by 213 days.

(21) Appl. No.: 18/374,560

(22) Filed: Sep. 28, 2023

(65) Prior Publication Data

US 2025/0107757 A1 Apr. 3, 2025

(51) Int. Cl.
*G16H 40/67* (2018.01)
*A61B 5/00* (2006.01)
(52) U.S. Cl.
CPC .......... *A61B 5/7228* (2013.01); *A61B 5/7225* (2013.01); *A61B 5/7475* (2013.01); *G16H 40/67* (2018.01); *A61B 5/681* (2013.01)
(58) Field of Classification Search
CPC .......... A61B 2560/0487; A61B 5/0533; A61B 5/332; A61B 5/369; A61B 5/389; A61B 5/681; A61B 5/7225; A61B 5/7228; A61B 5/7278; A61B 5/7475; G16H 40/67
See application file for complete search history.

(56) References Cited

U.S. PATENT DOCUMENTS

| | | |
|---|---|---|
| 5,483,261 A | 1/1996 | Yasutake |
| 5,488,204 A | 1/1996 | Mead et al. |
| 5,825,352 A | 10/1998 | Bisset et al. |
| 5,835,079 A | 11/1998 | Shieh |

(Continued)

FOREIGN PATENT DOCUMENTS

| | | |
|---|---|---|
| CN | 109497993 | 3/2019 |
| CN | 110794666 | 2/2020 |

(Continued)

OTHER PUBLICATIONS

Voica et al., "Dry-electrode based ECG monitoring device with electrodes reliability test capabilities," 2020 IEEE 8th Electronics System-Integration Technology Conference (ESTC), Sep. 2020, 6 pages.

(Continued)

*Primary Examiner* — George Manuel

(74) *Attorney, Agent, or Firm* — Brownstein Hyatt Farber Schreck, LLP

(57) ABSTRACT

A device includes a physiological sensor having a plurality of sensing electrodes, and a signal combining chip having a plurality of input channels, a waveform generator, a summing circuit, and an output channel. The plurality of input channels are configured to receive a plurality of voltage signals. Each input channel is configured to receive a respective one of the plurality of voltage signals from a respective one of the plurality of sensing electrodes. The waveform generator is configured to generate a set of modulation signals, each of which modulates a corresponding voltage signal of the plurality of voltage signals to generate a corresponding encoded voltage signal and form a set of encoded voltage signals. The summing circuit is configured to superimpose the set of encoded voltage signals to form a combined voltage signal that is outputted through the output channel.

20 Claims, 5 Drawing Sheets

(56)                References Cited

U.S. PATENT DOCUMENTS

| | | | |
|---|---|---|---|
| 5,880,411 | A | 3/1999 | Gillespie et al. |
| 6,188,391 | B1 | 2/2001 | Seely et al. |
| 6,310,610 | B1 | 10/2001 | Beaton et al. |
| 6,323,846 | B1 | 11/2001 | Westerman et al. |
| 6,496,721 | B1 | 12/2002 | Yonce |
| 6,690,387 | B2 | 2/2004 | Zimmerman et al. |
| 7,015,894 | B2 | 3/2006 | Morohoshi |
| 7,184,064 | B2 | 2/2007 | Zimmerman et al. |
| 7,197,351 | B2 | 3/2007 | Umeda et al. |
| 7,528,753 | B2 | 5/2009 | Chang |
| 7,616,110 | B2 | 11/2009 | Crump et al. |
| 7,663,607 | B2 | 2/2010 | Hotelling et al. |
| 7,834,795 | B1 | 11/2010 | Dudgeon et al. |
| 8,219,187 | B2 | 7/2012 | Sarkela |
| 8,301,232 | B2 | 10/2012 | Albert et al. |
| 8,378,811 | B2 | 2/2013 | Crump et al. |
| 8,479,122 | B2 | 7/2013 | Hotelling et al. |
| 8,618,930 | B2 | 12/2013 | Papadopoulos et al. |
| 9,042,973 | B2 | 5/2015 | Chen et al. |
| 9,044,171 | B2 | 6/2015 | Venkatraman et al. |
| 9,351,653 | B1 | 5/2016 | Harrison |
| 9,402,559 | B2 | 8/2016 | Imai et al. |
| 10,512,407 | B2 | 12/2019 | Richards et al. |
| 10,905,334 | B2 | 2/2021 | Van Den Ende et al. |
| 10,945,663 | B2 | 3/2021 | Bozkurt et al. |
| 11,026,628 | B1 | 6/2021 | Bruinsma et al. |
| 11,275,405 | B2 | 3/2022 | Hotelling |
| 11,291,380 | B2 | 4/2022 | Breen et al. |
| 11,311,217 | B2 | 4/2022 | Ajemba et al. |
| 11,523,775 | B2 | 12/2022 | Villafranca |
| 11,857,341 | B2 | 1/2024 | Bruinsma et al. |
| 12,377,215 | B1 | 8/2025 | Bibian et al. |
| 2013/0274583 | A1 | 10/2013 | Heck |
| 2013/0286653 | A1 | 10/2013 | Holman et al. |
| 2014/0107457 | A1 | 4/2014 | Raghunathan |
| 2015/0018660 | A1 | 1/2015 | Thomson et al. |
| 2015/0297145 | A1 | 10/2015 | Luna et al. |
| 2015/0359491 | A1 | 12/2015 | Luna et al. |
| 2016/0135715 | A1 | 5/2016 | Seppa et al. |
| 2016/0252552 | A1 | 9/2016 | Rabinovich et al. |
| 2016/0344352 | A1 | 11/2016 | Chang et al. |
| 2017/0049352 | A1 | 2/2017 | Mirov |
| 2017/0312576 | A1 | 11/2017 | Natarajan et al. |
| 2021/0041538 | A1 | 2/2021 | Zheng et al. |
| 2021/0169420 | A1 | 6/2021 | Jung |
| 2021/0275102 | A1 | 9/2021 | Cho et al. |
| 2021/0290159 | A1 | 9/2021 | Bruinsma et al. |
| 2021/0353201 | A1 | 11/2021 | Albert et al. |
| 2021/0373683 | A1* | 12/2021 | Kremin .................. G06F 3/044 |
| 2022/0346718 | A1 | 11/2022 | Ono |
| 2022/0378354 | A1 | 12/2022 | Clotworthy |
| 2022/0409137 | A1 | 12/2022 | Powell et al. |
| 2023/0010168 | A1 | 1/2023 | Jung et al. |
| 2023/0088533 | A1 | 3/2023 | Ang et al. |
| 2023/0106329 | A1 | 4/2023 | Li et al. |
| 2023/0210426 | A1 | 7/2023 | Filfil |
| 2023/0329640 | A1 | 10/2023 | Biel et al. |
| 2024/0122540 | A1 | 4/2024 | Bruinsma et al. |
| 2025/0068239 | A1 | 2/2025 | Shui et al. |

FOREIGN PATENT DOCUMENTS

| | | |
|---|---|---|
| CN | 114638247 | 6/2022 |
| CN | 114831647 | 8/2022 |
| CN | 115270877 | 11/2022 |
| CN | 115363558 | 11/2022 |
| CN | 117393152 | 1/2024 |
| EP | 4151141 | 3/2023 |
| JP | 2000163031 | 6/2000 |
| JP | 2002342033 | 11/2002 |
| WO | WO 14/021886 | 2/2014 |
| WO | WO 18/085664 | 5/2018 |
| WO | WO 21/056669 | 4/2021 |

OTHER PUBLICATIONS

Wu et al., "Non-intrusive Human Vital Sign Detection Using mm Wave Sensing Technologies: A Review," *ACM Transactions on Sensor Networks*, vol. 20, No. 1, Article 16, Nov. 2023, 36 pages.

* cited by examiner

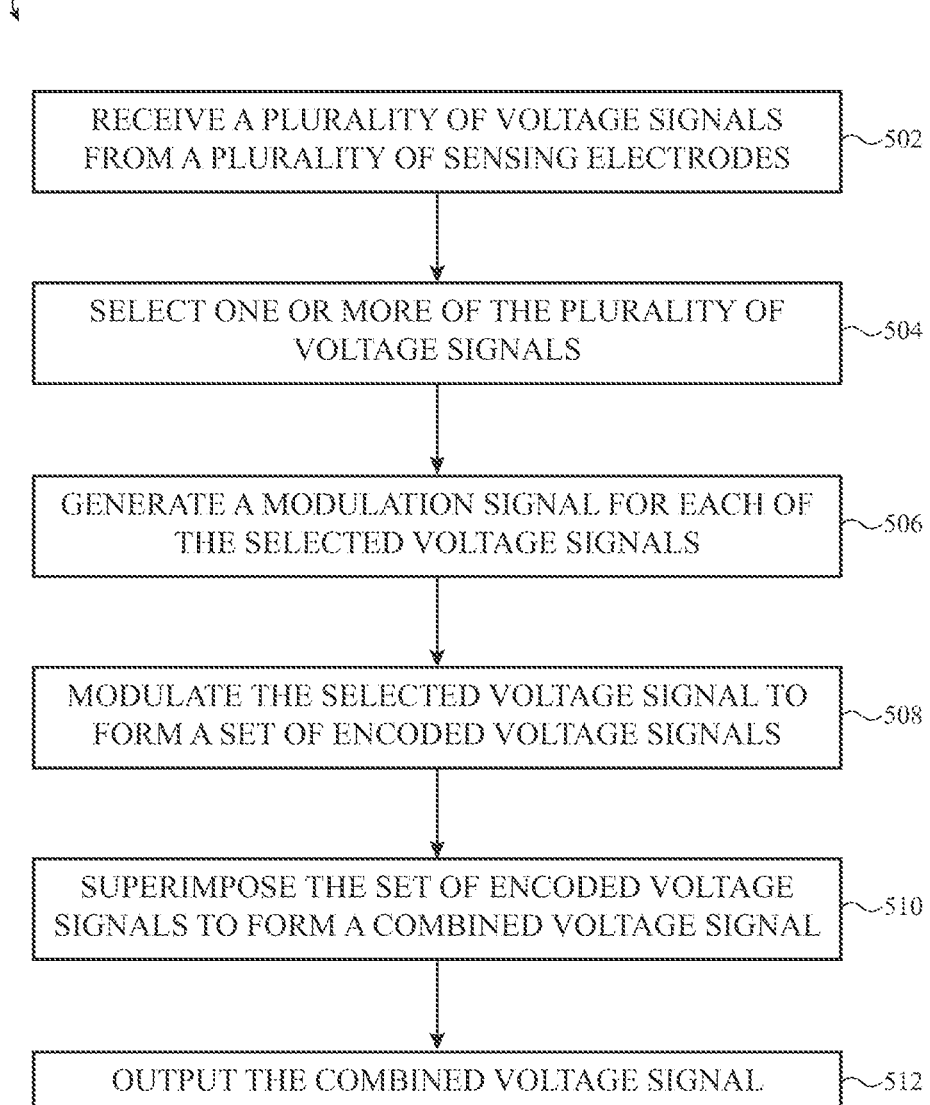

500

RECEIVE A PLURALITY OF VOLTAGE SIGNALS
FROM A PLURALITY OF SENSING ELECTRODES — 502

SELECT ONE OR MORE OF THE PLURALITY OF
VOLTAGE SIGNALS — 504

GENERATE A MODULATION SIGNAL FOR EACH OF
THE SELECTED VOLTAGE SIGNALS — 506

MODULATE THE SELECTED VOLTAGE SIGNAL TO
FORM A SET OF ENCODED VOLTAGE SIGNALS — 508

SUPERIMPOSE THE SET OF ENCODED VOLTAGE
SIGNALS TO FORM A COMBINED VOLTAGE SIGNAL — 510

OUTPUT THE COMBINED VOLTAGE SIGNAL — 512

*FIG. 5*

PHYSIOLOGICAL SENSORS WITH COMBINED SIGNAL OUTPUTS

FIELD

The described embodiments relate generally to processing analog signals received from a physiological sensor. More particularly, the present embodiments relate to systems and methods of using a signal combining chip to combine voltage signals from multiple electrodes generate a combined analog output signal.

BACKGROUND

Electrodes may be used as part of wearable devices (e.g., smartwatches) to measure electric potentials of a user. For example, electrocardiogram (ECG) measurements can use electrodes that contact a user's body to measure cardiac electrical activity. Similarly, electromyography (EMG) and electroencephalography (EEG) measurements can use electrodes to measure muscle and brain activity, respectively.

Traditional electrodes, which may be referred to as "wet electrodes," include an electrically conductive gel to facilitate electrical conduction from the skin. Electrodes may be incorporated into wearable devices such as a smartwatch, which may be used to continuously or periodically monitor the electrical potentials of a user. It may be desirable to utilize "dry electrodes," which do not require an electrically conductive gel, in wearable device such as a smartwatch. Dry electrodes, however, typically have relatively high impedance that may result in greater signal attenuation when measuring a voltage signal from a user's skin. Accordingly, it would be desirable to have a mechanism that can process these voltage signals in a manner that accounts for this impedance.

SUMMARY

Described herein are devices for processing signals from physiological sensors. The device includes a physiological sensor having a plurality of sensing electrodes, and a signal combining chip having a plurality of input channels, a waveform generator, a summing circuit, and an output channel. The plurality of input channels are configured to receive a plurality of voltage signals. Each input channel is configured to receive a respective one of the plurality of voltage signals from a respective one of the plurality of sensing electrodes. The waveform generator is configured to generate a set of modulation signals. Each of the set of modulation signals is applied to a corresponding voltage signal of the plurality of voltage signals to generate a corresponding encoded voltage signal and form a set of encoded voltage signals. The summing circuit is configured to superimpose the set of encoded voltage signals to form a combined voltage signal. The output channel is configured to output the combined voltage signal.

Other embodiments of this disclosure are directed to a method of processing a plurality of voltage signals received from a plurality of sensing electrodes of a physiological sensor. Specifically, a signal combining chip receives a plurality of voltage signals measured by the plurality of sensing electrodes. Each voltage signal corresponds to a respective one of the plurality of sensing electrodes. A set of voltage signals is selected from the plurality of voltage signals is then selected with a scan controller. A set of modulation signals corresponding to the selected set of voltage signals is generated using a waveform generator.

Each modulation signal of the set of modulation signals is used to modulate a corresponding selected voltage signal to form a corresponding encoded voltage signal of a set of encoded voltage signals. The set of encoded voltage signals are superimposed, using a summing circuit, to form a combined voltage signal. The combined voltage signal is outputted at an output channel of the signal combining chip.

In addition to the example aspects and embodiments described above, further aspects and embodiments will become apparent by reference to the drawings and by study of the following description.

BRIEF DESCRIPTION OF THE DRAWINGS

The disclosure will be readily understood by the following detailed description in conjunction with the accompanying drawings, wherein like reference numerals designate like structural elements, and in which:

FIG. 5 shows a block diagram for a method of processing a plurality of voltage signals to produce a combined voltage signal, as described herein.

Figure 1A:
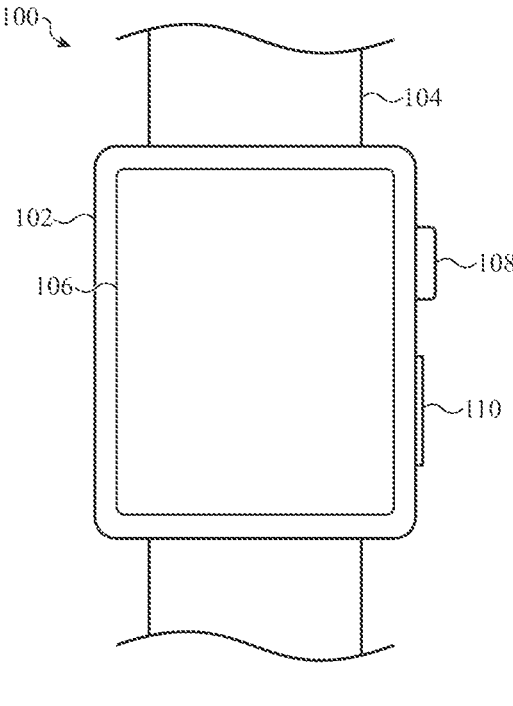
FIG. 1A shows a front view of an example electronic device that can be used to perform physiological measurements, as described herein.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

Directional terminology, such as "top," "bottom," "upper," "lower," "front," "back," "over," "under," "above," "below," "left," "right," "vertical," "horizontal," etc. is used with reference to the orientation of some of the components in some of the figures described below, and is not intended to be limiting. Because components in various embodiments can be positioned in a number of different orientations, directional terminology is used for purposes of illustration to demonstrate the relative orientation between components of the systems and devices described herein. The directional terminology is intended to be construed broadly, and therefore should not be interpreted to preclude components being oriented in different ways.

Described herein are physiological sensors that are designed to capture one or more physiological signals using a plurality of electrode. These electrodes (referred to herein as "sensing electrodes") may be positioned in contact with a user's body and may be used to generate a corresponding set of voltage signals. These voltage signals may be analyzed (e.g., using a processor) to determine one or more physiological parameters of a user. For example, the voltage signals may be measured to perform an ECG measurement, an EMG measurement, an EEG measurement, a galvanic skin response (GSR) measurement, combinations thereof, or the like.

The physiological sensors may be incorporated into a wearable device such as a smartwatch, and may utilize dry electrodes as the sensing electrodes. The use of dry sensing electrodes results in relatively high contact impedance (e.g., as compared to wet electrodes) as these sensing electrodes are placed in contact with a user's body. This high contact impedance, if not mitigated, may reduce the signal amplitude, and thereby reduce the signal-to-noise ratio (SNR). Accordingly, it may be desirable to buffer the voltage signals as close as possible to the body-electrode interface in order to reduce the impedance.

Space in wearable devices comes at a premium, and in many instances space may be especially limited nearby the sensing electrodes. There may not be sufficient space to buffer, digitize, and process these voltage signals in close proximity to the sensing electrode, which may negatively impact the SNR of measurements performed using the sensing electrodes. Accordingly, the physiological sensors described herein include a signal combining chip that combines multiple voltage signals into a singled combined analog output signal. The combined analog output signal may be buffered and output using a single electrical trace. Accordingly, the signal combining chip provides a space-efficient solution for buffering multiple voltage signals measured by the physiological sensor.

To generate the combined analog output signal, the signal combining chip may modulated a set of voltage signals using a modulation technique and combining the modulated signals into a common analog output signal. While the examples discussed herein are directed code-based multiple access modulation technique (e.g., a code division multiple access technique), other modulation techniques (e.g., a frequency division multiple access technique, or the like) may alternatively be used to combine the set of voltage signals. Specifically, the signal combining chip receives each voltage signal from a respective sensing electrodes through a corresponding input channel of the signal combining chip. The signal combining chip is configured to generate, for each voltage signal, a respective modulation signal that is used to modulate an amplitude of that voltage signal and thereby generate an encoded signal. Collectively, the signal combining chip may generate a set of modulation signals that are applied to a set of voltage signals to generate a set of encoded signals. The encoded signals are superimposed (e.g., by a summing circuit) to form a combined voltage signal that retains the information carried by the individual voltage signals.

Specifically, the set of modulation signals may be selected such that combined voltage signal, at any given point in time, includes information from a different selection of the voltage signals. For example, the selection may include a single voltage signal (e.g., corresponding to a single sensing electrode), multiple summed voltage signals (e.g., which may act to bin multiple electrodes), a differential voltage signal (e.g., which may represent a voltage differential between two sensing electrodes), or the like. In this way, the overall bandwidth of the combined voltage signal may be split between different selections of a plurality of voltage signals received from a plurality of sensing electrodes. Because the physiological parameters measured by the sensing electrodes may have relatively low frequency (e.g., less than 1 KHz), the voltage signals may be combined while still allowing the physiological sensor to adequately measure this low frequency content.

The combined voltage signal may also be buffered to reduce impedance, and the use of a single buffer may reduce size of the signal combining chip as compared to instances in which each voltage signal is individually buffered. The combined voltage signal may be outputted through an output channel of the signal combining chip. In this way, the combined voltage signal may be carried along a single electrical trace, which provide further space savings.

A signal processing chip may receive and digitize the combined voltage signal, and may demodulate the digitized signal to generate a set of demodulated signals corresponding to the set of encoded signals. The demodulated signals may be analyzed to determine one or more physiological parameters of the user. Additionally, noise that may be introduced to the combined voltage signal between the signal combining chip and the signal processing chip may appear as common mode noise at the signal processing chip, and may be removed during the generation and analysis of the demodulated signals. In some instances the signal processing chip may send one or more control signals to the signal combining chip, which may be used by the signal combining chip to dynamically adjust the operation of the signal combining chip. For example, SNR information of the individual demodulated signals may be calculated, and may be used to dynamically adjust the modulation signals generated by the waveform generator.

These and other embodiments are discussed below with reference to FIGS. 1A-5. However, those skilled in the art will readily appreciate that the detailed description given herein with respect to these Figures is for explanatory purposes only and should not be construed as limiting.

Figure 1B:
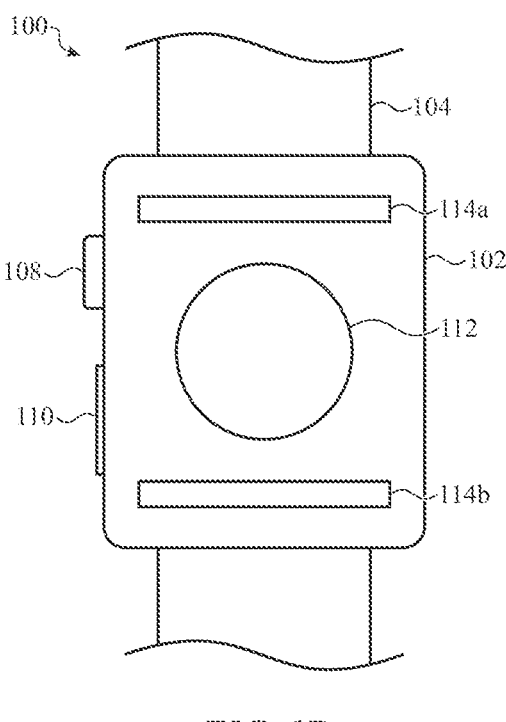
FIG. 1B shows a back view of an example electronic device that can be used to perform physiological measurements, as described herein.

FIG. 1A shows a front view of an example electronic device 100 and FIG. 1B shows a back view of the example electronic device 100 which can be used to perform physiological measurements, as described herein. The electronic device 100 is depicted as a watch, though this is merely one example embodiment of an electronic device, and the concepts discussed herein may apply equally or by analogy to other electronic devices, including mobile phones (e.g., smartphones), tablet computers, notebook computers, head-mounted displays, headphones, earbuds, digital media players (e.g., mp3 players), wearable bands, rings, or the like.

The device 100 includes a housing 102 and a band 104 coupled to the housing. The housing 102 may at least partially define an internal volume in which components of the device 100 may be positioned. The housing 102 may also define one or more exterior surfaces of the device, such as all or a portion of one or more side surfaces, a rear surface, a front surface, and the like. The housing 102 may be formed of any suitable material, such as metal (e.g., aluminum, steel, titanium, or the like), ceramic, polymer, glass, or the like.

The band 104 may attach the device 100 to a user, such as to the user's arm or wrist. The device 100 may include battery charging components within the device 100, which may receive power, charge a battery of the device 100, and/or provide direct power to operate the device 100 regardless of the battery's state of charge (e.g., bypassing the battery of the device 100). The device 100 may include a magnet, such as a permanent magnet, that magnetically couples to a magnet (e.g., a permanent magnet, electromagnet) or magnetic material (e.g., a ferromagnetic material such as iron, steel, or the like) in a charging dock (e.g., to facilitate wireless charging of the device 100).

The electronic device 100 can include a display 106. The display 106 can be positioned at least partially within the housing 102. The display 106 may define an output region in which graphical outputs are displayed. Graphical outputs may include graphical user interfaces, user interface elements (e.g., buttons, sliders, etc.), text, lists, photographs, videos, or the like. In some cases, the display 106 may output a graphical user interface with one or more graphical objects that display information collected from or derived from one or more sensors. For example, the display 106 may output one or more physiological paraments, such as ECG parameters that were measured for a user.

The display 106 may include or be associated with touch sensors and/or force sensors that extend along the output region of the display and which may use any suitable sensing elements and/or sensing techniques. Using touch sensors, the electronic device 100 may detect touch inputs applied to the cover, including detecting locations of touch inputs, motions of touch inputs (e.g., the speed, direction, or other parameters a gesture applied to the cover can generate), or the like. Using force sensors, the electronic device 100 may detect amounts or magnitudes of force associated with touch events applied to the cover. The touch and/or force sensors may detect various types of user inputs to control or modify the operation of the electronic device 100, including taps, swipes, multiple finger inputs, single- or multiple-finger touch gestures, presses, and the like.

The electronic device 100 may also include one or more user inputs such as a first input device 108 having a cap, crown, protruding portion, or component(s) or feature(s) positioned along a side surface of the housing 102. At least a portion of the first input device 108 (such as a crown body) may protrude from, or otherwise be located outside, the housing 102, and may define a generally circular shape or circular exterior surface. The exterior surface of the first input device 108 may be textured, knurled, grooved, or otherwise have features that may improve the tactile feel of the first input device 108 and/or facilitate rotation sensing.

The first input device 108 may facilitate a variety of potential interactions. For example, the first input device 108 may be rotated by a user (e.g., the crown may receive rotational inputs). Rotational inputs of the first input device 108 may zoom, scroll, rotate, or otherwise manipulate a user interface or other object displayed on the display 106 among other possible functions. The first input device 108 may also be translated or pressed (e.g., axially) by the user. Translational or axial inputs may select highlighted objects or icons, cause a user interface to return to a previous menu or display, or activate or deactivate functions among other possible functions.

In some cases, the electronic device 100 may sense touch inputs or gestures applied to the first input device 108, such as a finger sliding along the body of the first input device 108 (which may occur when first input device 108 is configured to not rotate) or a finger touching the body of the first input device 108. In such cases, sliding gestures may cause operations similar to the rotational inputs, and touches on a cap or crown may cause operations similar to the translational inputs. As used herein, rotational inputs include both rotational movements of the first input device 108, as well as sliding inputs that are produced when a user slides a finger or object along the surface of a crown in a manner that resembles a rotation (e.g., where the crown is fixed and/or does not freely rotate).

The electronic device 100 may also include other input devices, switches, buttons, or the like. For example, the electronic device 100 includes a second input device 110, which may be a button. The second input device 110 may be a movable button or a touch-sensitive region of the housing 102. The button may control various aspects of the electronic device 100. For example, the button may be used to select icons, items, or other objects displayed on the display 106, to activate or deactivate functions (e.g., to silence an alarm or alert), or the like.

FIG. 1B shows a rear side of the device 100. The electronic device 100 may include one or more windows 112 (one of which is shown) that allow light to pass through a portion of the housing 102. The one or more windows 112 may be coupled to the housing 102. The one or more windows 112 may include light transmissive materials and be associated with internal sensor components, which may be used to determine biometric information of a user, such as heart rate, blood oxygen concentration, or the like, as well as information such as a distance from the device to the user's skin or another object. The particular arrangement of the one or more windows 112 in the housing 102 shown in FIG. 1B is one example arrangement, and other window arrangements (including different numbers, sizes, shapes, and/or positions of the windows) are also contemplated.

The housing 102 may also include one or more electrodes 114a, 114b (collectively electrodes 114). The electrodes 114 may be part of a physiological sensor as described herein, and may facilitate the measurement of a set of voltage signals by the physiological sensor. Each of the electrodes 114 may be a conductive surface that is conductively coupled, via one or more components of the device 100, to a signal combining circuit as described herein. In some cases, one or more input devices (e.g., the first input device 108 and/or the second input device 110) may be operated as an electrode as part of the physiological sensor.

Figure 2:
FIG. 2 shows an example block diagram for an electronic device that can be used to perform physiological measurements, as described herein.
Figure 2:
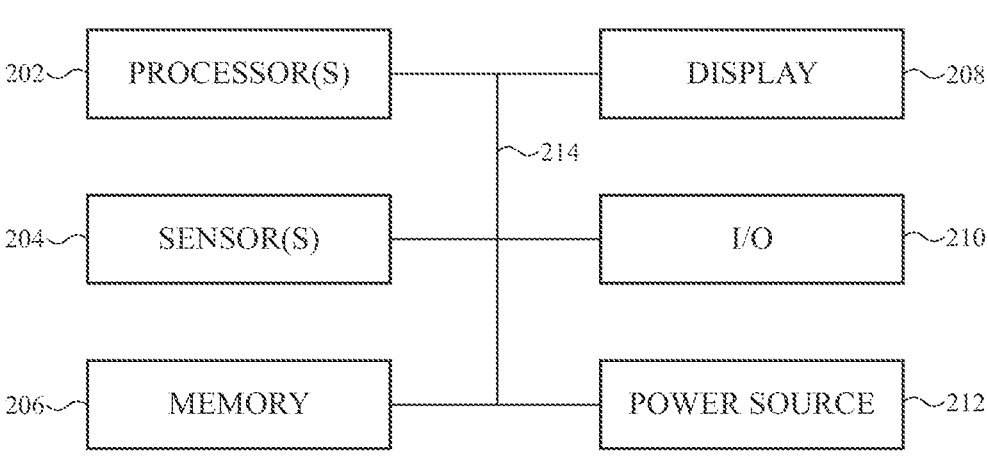

FIG. 2 shows an example block diagram 200 for an electronic device that can be used to perform physiological measurements, as described herein. The electronic device 200 can include a processor 202, one or more sensors 204, memory 206, a display 208, an input/output (I/O) mechanism 210, and a power source 212. Any of the components may be implemented as part of the device 100 of FIGS. 1A and 1B.

The processor 202 can control some or all of the operations of the electronic device 200. The processor 202 can communicate, either directly or indirectly, with some or all of the components of the electronic device 200. For example, a system bus or other communication mechanism 216 can provide communication between, the processor 202, the one or more sensors 204, the memory 206, the display 208, the input/output (I/O) mechanism 210, and the power source 212.

The processor 202 can be implemented as any electronic device capable of processing, receiving, or transmitting data or instructions. For example, the processor 202 can be a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitable computing element or elements.

It should be noted that the components of the electronic device 200 can be controlled by multiple processors. For example, select components of the electronic device 200 (e.g., a sensor 204) may be controlled by a first processor and other components of the electronic device 200 (e.g., the I/O mechanism 210) may be controlled by a second processor, where the first and second processors may or may not be in communication with each other.

The electronic device 200 may also include one or more sensors 204 positioned almost anywhere on the electronic device 200. The sensor(s) 204 can be configured to sense one or more type of parameters, such as but not limited to, electrical signals, pressure, sound, light, touch, heat, movement, relative motion, biometric data (e.g., physiological parameters), and so on. For example, the sensor(s) 204 may include a pressure sensor, an auditory sensor, a heat sensor, a position sensor, a light or optical sensor, an accelerometer, a pressure transducer, a gyroscope, a magnetometer, one or more physiological sensors, and so on. For example, the electronic device 200 may include a physiological sensor that includes one or more sensing electrode, such as described in more detail herein.

The memory 206 can store electronic data that can be used by the electronic device. For example, the memory 206 can store electrical data or content such as, for example, measured electrical signals, audio and video files, documents and applications, device settings and user preferences, timing signals, control signals, and data structures or databases. The memory 206 can be configured as any type of memory. By way of example only, the memory 206 can be implemented as random access memory, read-only memory, Flash memory, removable memory, other types of memory storage elements, or combinations of such devices.

The electronic device 200 may also include a display 208. The display 208 may include a liquid-crystal display (LCD), organic light-emitting diode (OLED) display, light-emitting diode (LED) display, or the like. If the display 208 is an LCD, the display 208 may also include a backlight component that can be controlled to provide variable levels of display brightness. If the display 208 is an OLED or LED type display, the brightness of the display 208 may be controlled by modifying the electrical signals that are provided to display elements. The display 208 may correspond to any of the displays shown or described herein.

The I/O mechanism 210 can transmit and/or receive data from a user or another electronic device. An I/O mechanism 210 can include a display, a touch sensing input surface, one or more buttons (e.g., a graphical user interface "home" button), one or more cameras, one or more microphones or speakers, one or more ports, such as a microphone port, and/or a keyboard. Additionally or alternatively, an I/O device or port can transmit electronic signals via a communications network, such as a wireless and/or wired network connection. Examples of wireless and wired network connections include, but are not limited to, cellular, Wi-Fi, Bluetooth, IR, and Ethernet connections.

The power source 212 can be implemented with any device capable of providing energy to the electronic device 200. For example, the power source 212 may be one or more batteries or rechargeable batteries. Additionally or alternatively, the power source 212 can be a power connector or power cord that connects the electronic device 200 to another power source, such as a wall outlet.

Figure 3:
FIG. 3 shows a schematic view of a physiological sensor that includes a signal combining chip and a signal processing chip, as described herein.
Figure 3:
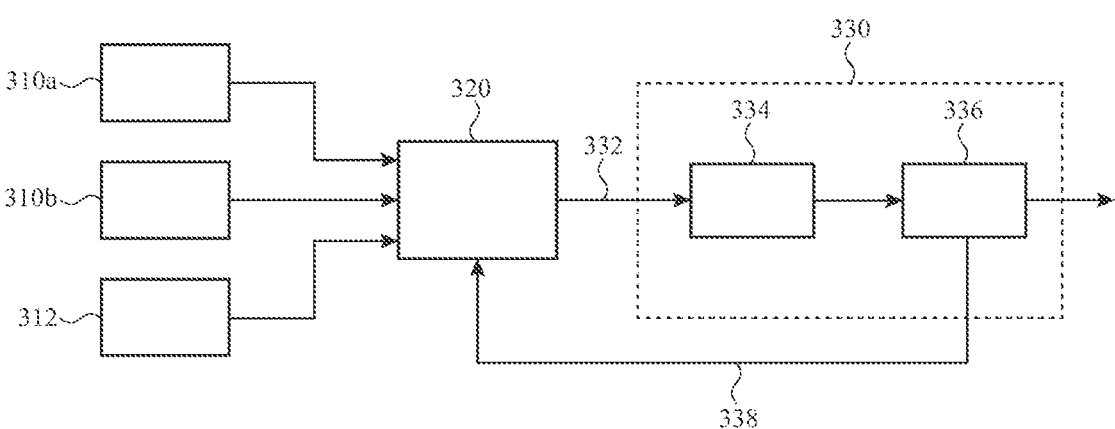

FIG. 3 shows a schematic view of an example physiological sensor 300 as described herein. Specifically, the physiological sensor 300 includes a plurality of electrodes (including a plurality of sensing electrodes 310a-310b, a signal combining chip 320, and a signal processing chip 330. The physiological sensor 300 may be incorporated into a wearable device or any other portable electronic device such as described herein, such as the electronic devices 100 and 200 described herein with respect to FIGS. 1A-2.

When the sensing electrodes 310a-310b are positioned into contact with a user's body, the plurality of sensing electrodes 310a-310b may measure a plurality of voltage signals that represent a plurality of electrical potentials associated with different portions of the user's body. Specifically, each sensing electrode measures a corresponding voltage signal of the plurality of voltage signals (e.g., a first sensing electrode 310a measures a first voltage signal, a second sensing electrode 310b may measure a second voltage signal, and so on). While the plurality of sensing electrodes 310a-310b is shown in FIG. 3 as having two sensing electrodes, it should be appreciated that the physiological sensor 300 may include any number (e.g., three, four, or five or more) of sensing electrodes as may be desired.

The plurality of sensing electrodes 310a-310b are electrically connected to the signal combining chip 320, thereby allowing the signal combining chip 320 to receive the plurality of voltage signals from the sensing electrodes 310a-310b. In some instances, the voltage signals may all be measured relative to a common reference. For example, the physiological sensor 300 may comprise a reference electrode 312. When the reference electrode 312 is placed in contact with the user, the voltage signals measured by the plurality of sensing electrodes 310a-310b may be measured relative to the reference electrode 312. In some instances, the reference electrode 312 may be electrically connected to the signal combining chip 320, which may connect the reference electrode 312 to a corresponding reference potential (e.g., ground) in the signal combining chip 320.

The signal combining chip 320 may process the voltage signals and combine them into a combined voltage signal 332. Details of the processes performed by the signal combining chip 320 are discussed in further detail with respect to FIG. 4. The combined voltage signal 332 may include information from each of the individual voltage signals, and may be outputted from the signal combining chip 320. In this way, a single, analog output signal may be used to carry information measured by the plurality of sensing electrodes 310a-310b to a signal processing chip 330, which may reduce the number of electrical traces needed to connect the signal combining chip 320 and the signal processing chip 330.

The combined voltage signal 332 outputted by the signal combining chip 320 is transmitted to a signal processing chip 330, which may digitize and analyze the combined voltage signal 332. The signal processing chip 330 may be a single application specific integrated circuit (ASIC) or be implemented across multiple ASICs and various components can be integrated on different ones of the multiple ASICs. The signal processing chip 330 includes a receiving channel for receiving the combined voltage signal. The signal processing chip further includes an analog-to-digital converter (ADC) 334 electrically coupled to the receiving channel and a digital signal processor (DSP) 336 electrically coupled to the ADC 334. The ADC 334 is configured to digitize the combined voltage signal transmitted thereto from the receiving channel. Accordingly, the ADC 334 generates a digital combined signal as an output, which includes information relating to each of the plurality of voltage signals. The digital combined signal is then transmitted to the DSP 336 for further processing.

The DSP 336 can perform one or more functions on the digital combined signal. For example, the DSP 336 may demodulate the digital combined signal to generate a corresponding digital signal associated with each of the voltage signals received from the sensing electrodes 310a-310b. The DSP 336 may also be configured to provide feedback to or otherwise control the signal combining chip 320. In some instances, a control trace 338 electrically connects the signal processing chip 330 and the signal combining chip 320, such that the DSP 336 may send control signals to the signal combining chip 320. For example, the DSP 336 may analyze one or more aspects of the demodulated digital signals (e.g., a signal-to-noise ratio of each digital signal) and may provide feedback to the signal combining chip 320 based on this analysis. Specifically, this feedback may be used to alter the operation of the signal combining chip 320, such as described in more detail herein.

Figure 4:
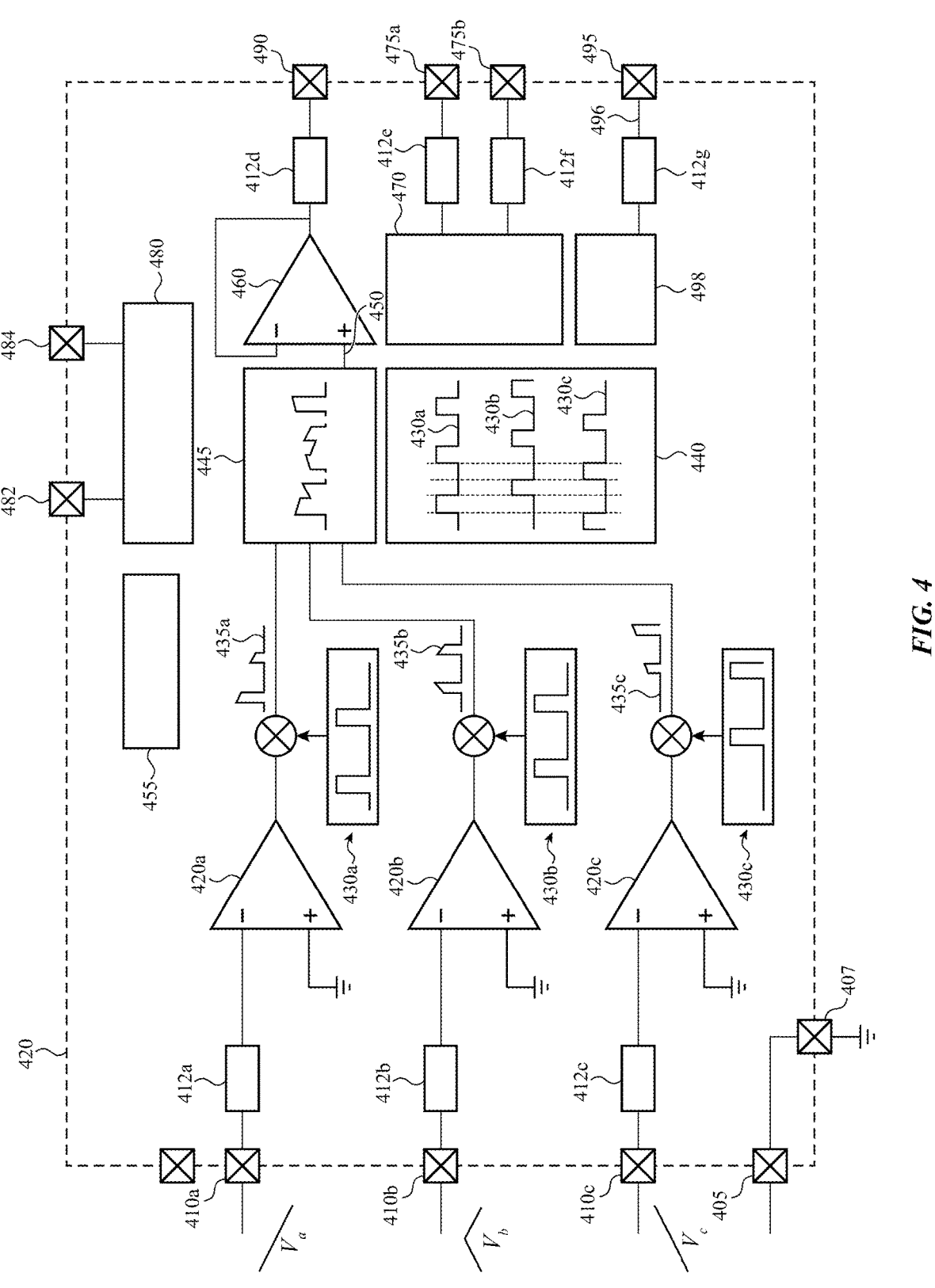
FIG. 4 shows a schematic view of a signal combining chip that may be used by the physiological sensors as described herein.

FIG. 4 shows a schematic view of a variation of the signal combining chip 320 that may be used as part of the physiological sensor 300 of FIG. 3. As shown there, the signal combining chip 320 has a plurality of input channels 410a-410c that are electrically connected to a plurality of sensing electrodes (not shown). The input channels 410a-410c receive a plurality of voltage signals $V_a$-$V_c$ measured by the plurality of sensing electrodes, such that each input channel receives a corresponding voltage signal. For example, in the variation shown in FIG. 4 a first input channel 410a may receive a first voltage signal $V_a$ from a first sensing electrode, a second input channel 410b may receive a second voltage signal $V_b$ from a second sensing electrode, and a third input channel 410c may receive a first voltage signal $V_c$ from a first sensing electrode.

In some variations, the signal combining chip 320 may include a first reference input channel 405 that may receive a reference potential from the physiological sensor 300. For example, the first reference input channel 405 may be electrically connected to a reference electrode, such that each of the plurality of voltage signals $V_a$-$V_c$ is measured relative to a reference potential provided by the reference electrode. In some variations, the first reference input channel 405 may be electrically connected to a second reference input channel 407. In these variations, multiple portions of the physiological sensor 300 (or portions of an electronic device incorporating the physiological sensor) may be referenced to a common potential. For example, the first reference input channel 405 may be electrically connected to a reference electrode, and the second reference input channel may be electrically connected to a system ground. In these instances, the reference electrode and the signal combining chip 320 may be tied to the system ground.

The signal combining chip 320 is configured to modulate some or all of the plurality of voltage signals $V_a$-$V_c$ to generate a set of encoded voltage signals 435a-435c. Specifically, the signal combining chip 320 includes a waveform generator 440 that is configured to generate a set of modulation signals 430a-430c. The waveform generator 440 may be any waveform generator that is configured to generate a set of modulation signals as described herein, such as will be readily understood by someone of ordinary skill in the art. In some variations, the waveform generator includes a phase lock loop (PLL) control system.

Each modulation signal is used to modulate a corresponding voltage signal to generate an encoded voltage signal. For example, in the variation shown in FIG. 4, the waveform generator 440 generates a first modulation signal 430a that may be multiplied with the first voltage signal $V_a$ to generate a first encoded voltage signal 435a, a second modulation signal 430b that may be multiplied with the second voltage signal $V_b$ to generate a second encoded voltage signal 435b, and a third modulation signal 430c that may be multiplied with the third voltage signal $V_c$ to generate a first encoded voltage signal 435c.

Each modulation signal may switch between two or more states according to a code-division multiple access scheme. For example, in some variation the set of modulation signals 430a-430c are generated using binary access codes. In these instances, each modulation signal may alternate between a first state with zero amplitude and a second state with a non-zero amplitude. When a modulation signal is used multiplied with a voltage signal to generate an encoded signal, the encoded signal will have a zero output when the modulation signal is in the first state and has a non-zero output (which may be proportional to the value of the voltage signal) when the modulation is in the second state.

In some of these variations, the set of modulation signals may be generated as a set of orthogonal signals. Specifically, each modulation signal may alternate between the first state and the second state according to a common modulation frequency and a different phase. At any given time, only one of the set of modulation signals 430a-430c has a non-zero amplitude. Accordingly, at any given time, only one of the encoded voltage signals 435a-435c has a non-zero amplitude. In this way, when the encoded voltage signals 435a-435c are combined (e.g., into a combined voltage signal 450), the resulting combined voltage signal 450 will include information from different sensing electrodes at different times.

It should be appreciated, however, that the signal combining chip 320 may be configured to generate non-orthogonal signals. For example, in some instances it may be desirable to sum the voltages signals from multiple electrodes and/or measure a voltage differential between different electrodes as part of measurement performed by the physiological sensor. In these instances, the waveform generator 440 may be configured to generate the set of modulation signals 430a-430c such that multiple modulation signals may concurrently have non-zero amplitudes at a given point in time. For example, if two modulation signals (e.g., the first modulation signal 430a and the second modulation signal 430b) are concurrently (e.g., during a first measurement window) in the second state such that each of these modulation signals has a non-zero amplitude, the resulting encoded voltage signals (e.g., the first encoded voltage signal 435a and the second encoded voltage signal 435b) will concurrently have non-zero amplitudes. When these encoded voltage signals are combined, at least a portion of the combined voltage signal 450 (e.g., corresponding to the first measurement window) will include information that represents the sum of two voltage signals (e.g., the first voltage signal $V_a$ and the second voltage signal $V_b$).

To generate a differential measurement between two sensing electrodes, the waveform generator 440 may be configured to generate the set of modulation signals 430a-430c using bipolar access codes. In these instances, some or all of the modulation signals may switch between a set of states that includes a first state having a first non-zero amplitude (e.g., a positive amplitude) and a second state having a second non-zero amplitude (e.g., a negative amplitude). In some instances the set of states may further include a third state having a zero amplitude. In order for the combined voltage signal to reflect the measurement of a single electrode at a given moment in time, only one of the modulation signals will have a non-zero amplitude (e.g., in the first state or the second state) at that time. Similarly, in order for the combined voltage signal to reflect a sum of two or more electrodes at another point in time, two or more modulation signals will concurrently have the same non-zero amplitude.

In instances where it is desirable for the combined voltage signal to reflect a differential between two electrodes, one modulation signal will be in a state that has a positive amplitude (e.g., the first state) while another modulation signal is concurrently in a state that has a negative amplitude (e.g., the second state). For example, during a first measurement window the first modulation signal 430a may be in a first state with a positive amplitude, such that the first encoded voltage signal 435a has a positive amplitude. During the first measurement window, the second modulation signal 430b may be in a second state with a negative amplitude, such that the second encoded voltage signal 435b has a negative amplitude. When the first and second encoded voltage signals 435a, 435b during the first time period, the resulting combined voltage signal may represent a differential between the first voltage signal $V_a$ and the second voltage signal $V_b$.

Overall, the set of modulation signals 430a-430c may be configured such that the combined voltage signal 450 alternates between a set of different measurement states, where each measurement state represents a different voltage signal or combination of voltage signals measured by a corresponding sensing electrode or plurality of sensing electrodes. The set of modulation signals 430a-430c at least partially control the measurement state of the combined voltage signal at any given moment in time. For example, the set of modulation signals 430a-430c shown in FIG. 4 may be used to generate a combined voltage signal 450 that alternates between three measurement states. Specifically, during a first measurement window the combined voltage signal 450 may include a first measurement state that represents the first voltage signal $V_a$ during the first measurement window. During a second measurement window, the combined voltage signal 450 may include a second measurement state that represents the second voltage signal $V_b$ during the second measurement window. During a third measurement window, the combined voltage signal 450 may include a third measurement state that represents the first voltage signal $V_c$ during the first measurement window. The combined voltage signal 450 may continue to alternate between these measurement states over the course of a physiological measurement.

The combined voltage signal 450 may be generated with any set of measurement states as may be desired. In some variations, the set of measurement states may be fixed. In these instances, the waveform generator 440 may be configured to generate a set of modulation signals 430a-430c that is fixed over time. In other variations, the signal combining chip 320 may be configured to dynamically update the set of modulation signals 430a-430c, which may adjust the measurement states of the combined voltage signal 450. Updating the set of modulation signals 430a-430c may change the number, type, and/or relative duty cycle of one or more measurement states of the combined voltage signal 450.

Accordingly, in some variations the signal combining chip 320 may include a scan controller 455 that is configured to control the waveform generator 440 to alter the set of modulation signals 430a-430c generated by the waveform generator 440. In some instances it may be desirable to perform measurements using different combinations of sensing electrodes at different times. For example, a first physiological measurement (or portion of a physiological measurement) may utilize some or all of the sensing electrodes to generate a combined voltage signal that alternates between a first set of measurement statements. A second physiological measurement (or portion of a physiological measurement) may utilize some or all of the sensing electrodes to generate a combined voltage signal that alternates between a different second set of measurement states.

Specifically, the scan controller 455 to may update the set modulation signals 430a-430c to add and/or remove one or more measurement states. As a non-limiting example, during a first portion of a measurement that combined voltage signal may have three measurement states (e.g., a first measurement corresponding to the first voltage signal $V_a$, a second measurement state corresponding to the second voltage signal $V_b$, and a third measurement state corresponding to the third voltage signal $V_c$). During a second portion of the physiological measurement, the third measurement state may be replaced with a fourth measurement state (e.g., a sum of the first and second voltage signals $V_a$, $V_b$, or the like), such that the combined voltage signal 450 alternates between the first, second, and fourth measurement states. During a third portion of the physiological measurement, the fourth measurement state may be removed, such that the combined voltage signal alternates between the first and second measurement states.

In some instances, the scan controller 455 may update the set of modulation signals 430a-430c to dynamically reallocate the bandwidth of the combined voltage signal 450. For example, in some variations the set of modulation signals 430a-430c collective has a 100% duty cycle, such that at least one modulation signal 430a-430c has a non-zero amplitude at each moment in time. In this way, the combined voltage signal 450 may always include information from at least one of the plurality of voltage signals. In these instances, the relative duty cycles of the modulation signals 430a-430c may be altered as the number of measurement states changes. If a measurement state is removed, the duty cycle of one or more of the modulation signals 430a-430c may be increased. Similarly, if a new measurement state is added, the duty cycle of one or more of the modulation signals 430a-430c may be decreased.

In other variations, the set of modulation signals 430a-430c may be dynamically adjusted based on an analysis of the combined voltage signal. For example, the signal processing chip 330 may analyze the demodulated signals to determine a signal-to-noise ratio (SNR) or each demodulated signal. The signal processing chip 330 may control or otherwise provide feedback to the signal combining chip 320, and the signal combining chip 320 may update the relative duty cycles of modulation signals 430a-430c to adjust the relative duty cycles of the corresponding measurement states. For example, the signal processing chip 330 may increase the duty cycle of one or more measurement states having relatively lower SNR and decrease the duty cycle of one or more measurement states having relatively higher SNR.

To combine the set of encoded signals 435a-435c into the combined voltage signal 450, the signal processing chip 330 may include a summing circuit 445 that is configured to combine the set of encoded signals 435a-435c. The summing circuit 445 may include any suitable circuitry that is capable of combining multiple analog signals, as will be readily understood by someone of ordinary skill in the art. In some variations, the summing circuit 445 may include, for each input channel of the plurality of input channels 412a-412c, a respective switch (not shown) that may control whether a voltage signal measured by a giving sensing electrode is summed by the summing circuit 445. In this way, voltage signals that are not actively modulated by one of the set of modulation signals 430a-430c are not summed as part of generating the combined voltage signal 450. In these instances, the scan controller 455 may control operation of the summing circuit 445.

The combined voltage signal 450 may be outputted from the signal combining chip 320 via an output channel 490. In some variations, the signal combining chip 320 includes a buffer 460 positioned between the summing circuit 445 and the output channel 490. Accordingly, the buffer 460 may act to reduce impedance of the combined voltage signal 450 before leaving the signal combining chip.

In some variations, the signal combining chip 320 is configured to receive one or more control or data signals from other portions of the physiological sensor 300 or other portions of an electronic device incorporating the physiological sensor 300. For example, in some variations, the signal combining chip 320 may include a reference clock input 495 that is configured to receive a timing signal 496. For example, the timing signal 496 may be a reference clock signal received by the signal processing chip 330, so that the signal processing chip 330 and the signal combining chip 320 operate from a common timing signal. The timing signal 496 may be used by the scan controller 455 and/or the waveform generator 440 to generate the modulation signals 430a-430c. Instances, the signal combining chip 320 may include a clock jitter filter 498 that is configured to filter or otherwise attenuate jitter in the timing signal 496.

Additionally, or alternatively, the signal combining chip 320 may include digital interface driver 470 that is configured to receive one or more control signals that may be used by the scan controller 455 in controlling the waveform generator 440 and/or the summing circuit 445. Specifically, the digital interface driver 470 may include one or more control channels (e.g., a first control channel 475a and a second control channel 475b) that may receive one or more control signals. For example, in some variations the first and second control channels 475a, 475b may act as a serial data line and a serial clock line, respectively, of an I2C communication protocol.

In some variations, it may be desirable reduce noise associated with the combined voltage signal. For example, in some variations the signal combining chip 320 may include a plurality of active low pass filters 420a-420c positioned between the plurality of input channels 410a-410c and the summing circuit 445. Each active low pass filter may be positioned to filter a corresponding voltage signal (e.g., a first active low pass filter 420a is positioned to filter the first voltage signal $V_a$, a second active low pass filter 420b is positioned to filter the second voltage signal $V_b$, and so on). The active low pass filters may be configured to filter out signal content above an expected frequency of the physiological signals being measured.

In some variations the signal combining chip 320 may include one or more electromagnetic interference filters (EMIFs) that are configured to filter out currents that may be introduced into the channels of the signal combining chip 320 as a result of electromagnetic interference. For example, in FIG. 4 the signal combining chip 320 is shown as having a first plurality of EMIFs 412a-412c corresponding to the plurality of input channels 410a-410c, an EMIF 412d corresponding to output channel 490, and a second plurality of EMIFs 412e-412g corresponding to other inputs (e.g., the first and second control channels 475a, 475b and the reference clock input 495, respectively).

In order to power the signal combining chip 320, the signal combining chip 320 may include a power management interface 480 that receives power via one or more power supply inputs. For example, the power management interface 480 may include a first power supply input 482 that is connected to a first power supply. The power from the first power supply may be used to modulate the voltage signals $V_a$-$V_c$ as described herein, as well as to power other components of the signal combining chip 320. In some instances (such as when a binary access code is used to generate the set of modulation signals 430a-430c), the power management interface 480 may include a single power supply input. In other variations (such as when a bipolar access code is used to generate the set of modulation signals 430a-430c), the power management interface 480 may include multiple power supply inputs. For example, in the variation shown in FIG. 4, the power management interface 480 includes a first power supply input 482 (e.g., connected to a positive supply) and a second power supply input 484 (e.g., connected to a negative supply).

FIG. 5 shows a block diagram 500 for a method of processing a plurality of voltage signals received from a plurality of sensing electrodes of a physiological sensor. The method in block diagram 500 is executed by various components of a signal combining chip, such as the signal combining chip 320 described above with respect to FIG. 4. At block 502, a plurality of voltage signals are received that correspond to a plurality of sensing electrodes connected to the signal combining chip. Each voltage signal is measured by a respective sensing electrode that is positioned in contact with a user's body, and is received through a respective input channel of a plurality of input channels in the signal combining chip.

At block 504, one or more of the received plurality of voltage signals is selected. The voltage signals may be selected, based on various desired criteria, by a scan controller associated with the signal combining chip. Specifically, a set of voltage signals may be selected from the plurality of voltage signals, and the waveform generator to generate the set of modulation signals based on the selected set of voltage signals. In some embodiments, selecting one or more of the plurality of voltage signals may include assigning a weighted duty cycle to a respective one of the selected voltage signals.

At block 506, a set of modulation signals are generated by a waveform generator in the signal combining chip. Each modulation signal is used to modulate a respective one of the selected voltage signals. In some embodiments, each of the set of modulation signals alternates between zero amplitude in a first state and a non-zero amplitude in a second state according to a common modulation frequency and a different phase. In other embodiments, one or more of set of modulation signals may switch between a set of states that includes a first state having a first non-zero amplitude. Further, in some embodiments, the set of modulation signals may be generated based on one or more control signals received through a control channel in the signal combining chip. In some such embodiments, the assigned duty cycle of one or more of the modulation signals may be dynamically changed based on the one or more control signals. In other embodiments, the set of modulation signals may be generated using a timing signal received from a reference clock input in the signal combining chip such that the modulation of the voltage signals can be synchronized with a demodulation process downstream. In some embodiments, the set of modulation signals may be generated such that the modulation signals collectively have a 100% duty cycle during any time period when they are applied to the selected voltage signals.

At block 508, each modulation signal is applied to modulate the respective selected voltage signal and form a corresponding encoded voltage signal. Collectively, the set of modulation signals are applied to a set of voltage signals to generate a set of encoded voltage signals.

At block 510, the encoded voltage signals are superimposed, using a summing circuit, to form a combined voltage signal. The combined voltage signal may alternate between a set of different measurement states as described herein.

At block 512, the combined voltage signal is outputted through an output channel of the signal combining chip. In some variations, the combined voltage signal is buffered before being outputted through the output channel. In some variations, the combined voltage signal is transmitted to a signal processing chip. The signal processing chip receives the combined voltage signal through a receiving channel communicably coupled to the signal combining chip. The combined voltage signal is then converted to a digital combined signal by an analog-to-digital converter (ADC) in the signal processing chip. Subsequently, the digital combined signal is demodulated to generate a corresponding digital signal for each of the plurality of voltage signals received from the plurality of sensing electrodes.

The foregoing description, for purposes of explanation, uses specific nomenclature to provide a thorough understanding of the described embodiments. However, it will be apparent to one skilled in the art, after reading this description, that the specific details are not required in order to practice the described embodiments. Thus, the foregoing descriptions of the specific embodiments described herein are presented for purposes of illustration and description, and not limitation. They are not targeted to be exhaustive or to limit the embodiments to the precise forms disclosed. It will be apparent to one of ordinary skill in the art, after reading this description, that many modifications and variations are possible in view of the above teachings or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application. Numerous changes to the disclosed embodiments can be made in accordance with the disclosure herein, without departing from the spirit or scope of the disclosure. Thus, the breadth and scope of the present disclosure should not be limited by any of the above described embodiments. Rather, the scope of the disclosure should be defined in accordance with the following claims and their equivalents.

What is claimed is:

1. A device for measuring voltage signals comprising:
a physiological sensor comprising a plurality of sensing electrodes;
a signal combining chip comprising:
a plurality of input channels configured to receive a plurality of voltage signals from the plurality of sensing electrodes, wherein each input channel of the plurality of input channels is configured to receive a corresponding voltage signal of the plurality of voltage signals from a corresponding sensing electrode of the plurality of sensing electrodes;
a waveform generator configured to generate a set of modulation signals, wherein each of the set of modulation signals is applied to a corresponding voltage signal of the plurality of voltage signals to generate a corresponding encoded voltage signal of a set of encoded voltage signals;
a summing circuit configured to superimpose the set of encoded voltage signals to form a combined voltage signal; and
an output channel configured to output the combined voltage signal; and
a signal processing chip communicably coupled to the signal combining chip, the signal processing comprising:
a receiving channel configured to receive the combined voltage signal as an input; and
an analog-to-digital converter configured to digitize the combined voltage signal.

2. The device of claim 1, wherein each of the set of modulation signals alternates between zero amplitude in a first state and a non-zero amplitude in a second state according to a common modulation frequency and a different phase.

3. The device of claim 1, wherein:
the plurality of voltage signals comprises a first voltage signal and a second voltage signal;
the set of modulation signals comprises a first modulation signal that is applied to the first voltage signal and a second modulation signal that is applied to the second voltage signal;
the first modulation signal modulates, during a measurement window, the first voltage signal with a first non-zero amplitude at a first state to form a first encoded voltage signal; and
the second modulation signal modulates, during the measurement window, the second voltage signal with a second non-zero amplitude at a second state to form a second encoded voltage signal, such that the combined voltage signal corresponds during the measurement window to a differential voltage signal between the first encoded voltage signal and the second encoded voltage signal.

4. The device of claim 1, wherein the signal combining chip further comprises:
a controller configured to select a set of voltage signals from the plurality of voltage signals and control the waveform generator to select the set of modulation signals based on the selected set of voltage signals.

5. The device of claim 1, wherein the signal combining chip further comprises: a digital interface driver configured to receive one or more control signals through a control channel.

6. The device of claim 1, wherein the signal combining chip further comprises a buffer positioned between the summing circuit and the output channel.

7. The device of claim 1, wherein the signal combining chip further comprises an active low pass filter electrically coupled to a respective input channel.

8. The device of claim 1, wherein the signal combining chip further comprises a reference clock input configured to receive a timing signal that is used by the waveform generator to generate the set of modulation signals.

9. A method of processing a plurality of voltage signals received from a plurality of sensing electrodes of a physiological sensor, the method comprising:

receiving, at a signal combining chip, a plurality of voltage signals that are measured by the plurality of sensing electrodes, wherein each voltage signal of the plurality of voltage signals is measured by a corresponding sensing electrode of the plurality of sensing electrodes;

selecting, with a scan controller associated with the signal combining chip, a set of voltage signals from the plurality of voltage signals;

generating, using a waveform generator in the signal combining chip, a set of modulation signals corresponding to the selected set of voltage signals;

applying each modulation signal of the set of modulation signals to a corresponding selected voltage signal to form a corresponding encoded voltage signal of a set of encoded voltage signals;

superimposing the set of encoded voltage signals, using a summing circuit, to form a combined voltage signal;

outputting, at an output channel of the signal combining chip, the combined voltage signal receiving, through a receiving channel at a signal processing chip communicably coupled to the signal combining chip, the combined voltage signal;

digitizing, using an analog-to-digital converter at the signal processing chip, the combined voltage signal to generate a digital combined signal; and demodulating the digital combined signal to generate a corresponding digital signal for each of the plurality of voltage signals received from the plurality of sensing electrodes of the physiological sensor.

10. The method of claim 9, further comprising:

buffering the combined voltage signal before outputting the combined voltage.

11. The method of claim 9, wherein each of the set of modulation signals alternates between zero amplitude in a first state and a non-zero amplitude in a second state according to a common modulation frequency and a different phase.

12. The method of claim 9, wherein the combined voltage signal comprises, during a first measurement window, a differential voltage signal between a first selected voltage signal and a second selected voltage signal.

13. The method of claim 9, wherein selecting one or more of the plurality of voltage signals further comprises assigning a weighted duty cycle to a respective one of the selected voltage signals.

14. The method of claim 9, further comprising:

receiving one or more control signals through a control input channel.

15. The method of claim 14, further comprising:

changing a duty cycle of at least one of the set of modulation signals based on the received one or more control signals.

16. The method of claim 9, further comprising:

receive a timing signal that is used to generate the set of modulation signals.

17. The method of claim 9, further comprising:

generating the set of modulation signals such that set of modulation signals collectively has a 100% duty cycle.

18. A device for measuring voltage signals comprising:

a physiological sensor comprising a plurality of sensing electrodes; and a signal combining chip comprising:

a plurality of input channels configured to receive a plurality of voltage signals from the plurality of sensing electrodes, wherein each input channel of the plurality of input channels is configured to receive a corresponding voltage signal of the plurality of voltage signals from a corresponding sensing electrode of the plurality of sensing electrodes;

a waveform generator configured to generate a set of modulation signals, wherein each of the set of modulation signals is applied to a corresponding voltage signal of the plurality of voltage signals to generate a corresponding encoded voltage signal of a set of encoded voltage signals; and a summing circuit configured to superimpose the set of encoded voltage signals to form a combined voltage signal;

a digital interface driver configured to receive one or more control signals through a control channel; and an output channel configured to output the combined voltage signal.

19. The device of claim 18, wherein the signal combining chip is configured to change a duty cycle of at least one of the set of modulation signals based on the received one or more control signals.

20. The device of claim 18, wherein the signal combining chip further comprises:

a controller configured to select a set of voltage signals from the plurality of voltage signals and control the waveform generator to select the set of modulation signals based on the selected set of voltage signals.

* * * * *